United States Patent
Fieremans et al.

(10) Patent No.: US 9,916,654 B2
(45) Date of Patent: Mar. 13, 2018

(54) SYSTEM, METHOD AND COMPUTER ACCESSIBLE MEDIUMS FOR DETERMINING NEURODEGENERATION

(71) Applicants: NEW YORK UNIVERSITY, New York, NY (US); Els Fieremans, New York, NY (US); Dmitry S. Novikov, New York, NY (US)

(72) Inventors: Els Fieremans, New York, NY (US); Dmitry S. Novikov, New York, NY (US)

(73) Assignee: New York University, New York, NY (US)

( * ) Notice: Subject to any disclaimer, the term of this patent is extended or adjusted under 35 U.S.C. 154(b) by 459 days.

(21) Appl. No.: 14/358,785

(22) PCT Filed: Nov. 16, 2012

(86) PCT No.: PCT/US2012/065682
§ 371 (c)(1),
(2) Date: May 16, 2014

(87) PCT Pub. No.: WO2013/075030
PCT Pub. Date: May 23, 2013

(65) Prior Publication Data
US 2014/0314298 A1    Oct. 23, 2014

Related U.S. Application Data

(60) Provisional application No. 61/560,800, filed on Nov. 16, 2011.

(51) Int. Cl.
*G06K 9/00* (2006.01)
*G06T 7/00* (2017.01)
(Continued)

(52) U.S. Cl.
CPC ...... *G06T 7/0012* (2013.01); *G01R 33/56341* (2013.01); *G06K 9/00147* (2013.01);
(Continued)

(58) Field of Classification Search
None
See application file for complete search history.

(56) References Cited

U.S. PATENT DOCUMENTS 6,529,763 B1    3/2003  Cohen et al.
2003/0194427 A1   10/2003  Benja-Athon
(Continued)

OTHER PUBLICATIONS

Sen et al., "A model for diffusion in white matter in the brain", Biophysical Journal vol. 89, Nov. 2005.*
(Continued)

*Primary Examiner* — Soo Park
(74) *Attorney, Agent, or Firm* — Andrews Kurth Kenyon LLP

(57) ABSTRACT

Method, system and computer-accessible medium for determining at least one of axonal loss or myelin degradation can be provided. For example, it is possible to receive data based on at least one of a measure of diffusion of an axonal structure or a measure of a density of axons, and determine axonal loss and/or myelin degradation based on the data. The determination can be based on axonal geometry of at least one parallel tube.

33 Claims, 10 Drawing Sheets

(51) Int. Cl.
*G01R 33/563* (2006.01)
*A61B 5/055* (2006.01)
*G01R 33/56* (2006.01)
*G06F 19/00* (2018.01)

(52) U.S. Cl.
CPC .......... *A61B 5/055* (2013.01); *G01R 33/5608* (2013.01); *G06F 19/3437* (2013.01); *G06T 2207/10088* (2013.01); *G06T 2207/30024* (2013.01)

(56) References Cited

U.S. PATENT DOCUMENTS

| | | | |
|---|---|---|---|
| 2010/0074409 A1 | 3/2010 | John et al. | |
| 2011/0282183 A1* | 11/2011 | Song | G01R 33/56341 600/410 |

OTHER PUBLICATIONS

Balls et al., "A simulation environment for diffusion weighted MR experiments in complex media", Magn Reson Med. Sep. 2009 62(3).*
Fieremans et al., "White matter model for diffusional kurtosis imaging", ISMRM May 2010.*
Fieremans et al., "White matter characterization with diffusional kurtosis imaging", NeuroImage 58 (2011) 177-188.*
Fox et al., "Measuring myelin repair and axonal loss with diffusion tensor imaging", Jan. 2011.*
Traka et al., "A genetic mouse model of adult-onset, pervasive central nervous system demyelination with robust remyelination", Sep. 2010.*
Farrell et al., "q-Space and conventional diffusion imaging of axon and myelin damage in the rat spinal cord after axotomy", Magnetic Resonanace in Medicine 63: 1323-1335 (2010).*
Alexander et al., "Orientationally invariant indices of axon diameter and density from diffusion MRI", NeuroImage 52 (2010) 1374-1389.*
Hall et al., "Convergence and parameter choice for Monte-Carlo simulations of diffusion MRI", IEEE Transactions on Medical Imaging, vol. 28, No. 9, Sep. 2009.*
Song et al., "Diffusion tensor imaging detects and differentiates axon and myelin degeneration in mouse optic nerve after retinal ischemia", NeuroImage 20 (2003) 1714-1722.*
Bjartmar C et al. "Axonal loss in normal-appearing white matter in a patient with acute MS" Neurology 57, pp. 1248-1252 (2001).
Evangelou N et al. "Quantitative Pathological Evidence for Axonal Loss in Normal Appearing White Matter in Multiple Sclerosis" Ann. Neurology, 47;3, 391-395 (2000).
Brun A & Englund E. "A White Matter Disorder in Dementia of the Alzheimer Type: A Pathoanatomical Study" Ann. Neurology, 19;3, pp. 253-262 (1986).
Fieremans E et al. "Monte Carlo study of a two-compartment exchange model of diffusion" NMR Biomedicine, 23, pp. 711-724 (2010).
Fieremans E et al. "White matter characterization with diffusional kurtosis imaging" Neuroimage, 58 pp. 177-188 (2011).
Aboitiz F et al. "Fiber composition of the human corpus callosum" Brain Research, 598 pp. 143-153 (1992).
LL Latour et al, "Time-dependent diffusion of water in a biological model system" PNAS, 91 pp. 1229-1233 (1994).
DS Novikov & VG Kiselev, "Effective medium theory of a diffusion-weighted signal" NMR Biomedicine, 23 pp. 682-697 (2010).
Barazany D et al. "In vivo measurement of axon diameter distribution in the corpus callosum of rat brain" Brain, 132 pp. 1210-1220 (2009).
Klawiter E et al. "Radial diffusivity predicts demyelination in ex vivo multiple sclerosis spinal cords" Neuroimage, 55 pp. 1454-1460 (2011).
Smith SM et al. "Tract-based spatial statistics: Voxelwise analysis of multi-subject diffusion data" Neuroimage, 31 pp. 1487-1505 (2006).
Lazar M et al. "Mapping brain anatomical connectivity using white matter tractography" NMR Biomedicine, pp. 821-835 (2010).
International Search Report for International Patent Application No. PCT/US2012/065682 dated Mar. 14, 2013.
International Written Opinion for International Patent Application No. PCT/US2012/065682 dated Mar. 14, 2013.
Evanglou, N. et al., "Size-Selective Neuronal Changes in the Anterior Optic . . . ," Brain, vol. 124, pp. 1813-1820, 2001.
Garnett, J.C. MaxWell "Colours in Metal Glasses and in Metallic Films," Phil Trans R. Soc Lond, B203, pp. 385-420, Apr. 19, 1904.
Landauer, Rolf "Electrical Conductivity in Inhomogenous Media," AIP Conference Proceedings, vol. 40, No. 2, 1978.
Bruggeman, Von D.A.G., "Berechnung Verschiedener Physikalischer . . . ," Ann Phys. vol. 24, pp. 636-664, 1935.
Sen, P.N. et al., "A Self-Similar Model for Sedimentary Rocks with Application to the Dielectric . . . ," Geophysics, vol. 46, No. 6, pp. 781-795, May 1981.
Hashin, Z. et al., "A Variational Approach to the Theory of the Effective Magnetic . . . ," Journal of Applied Physics, vol. 33, No. 10, Oct. 1962.
Perrins, W.T. et al., "Transport Properties of Regular Arrays of Cyliders," Pro. R. Soc. Land., vol. A 369, pp. 207-225, 1979.

\* cited by examiner

SYSTEM, METHOD AND COMPUTER ACCESSIBLE MEDIUMS FOR DETERMINING NEURODEGENERATION

CROSS-REFERENCE TO RELATED APPLICATION(S)

The present application relates to and claims the benefit and priority from International Patent Application No. PCT/US2012/065682 filed Nov. 16, 2012, which claims the benefit of priority from U.S. Provisional Patent Application No. 61/560,800, filed on Nov. 16, 2011, the entire disclosures of which are incorporated herein by reference in their entireties.

FIELD OF THE DISCLOSURE

The present disclosure relates generally to exemplary systems, methods and computer accessible mediums for determining neurodegeneration, and more specifically, to determining axonal loss and myelin degradation based on tortuosity and axonal water fraction.

BACKGROUND INFORMATION

In neurodegeneration, the progressive loss of structure or function of neurons in the brain, there are many types of degeneration in brain white matter ("WM"). Two major types of degeneration include myelin degradation (e.g., demyelination and dysmyelination) and axonal loss, both of which are hallmarks of neurodegenerative diseases. In lay terms, myelin degradation can be characterized as a reduction of the thickness of the myelin sheath (a coaxial coating of an axon consisting of multiple lipid layers). Axonal loss can be characterized as the removal of an axon altogether, causing fluid to be substituted in its place. Axonal loss is considered to be the histological substrate for permanent disability, while myelin degradation, unlike axonal loss, can be reversible. Currently, however, there is no known non-invasive method for differentiating between axonal loss and myelin degradation.

Axonal loss and myelin degradation myelin degradation both include subtle microstructural changes affecting tissue microarchitecture at a micrometer length scale (e.g., a length scale of about 1000 times below the nominal resolution in millimeters of magnetic resonance imaging ("MRI") scanners). However, MRI is currently the only practically viable noninvasive probe for soft tissues. Thus, these subtle changes from axonal loss and myelin degradation myelin degradation can be well below the nominal spatial resolution that could ever be achieved in the foreseeable future, which presents a significant challenge to distinguish between, and to quantify the degree (e.g., relative to age-matched normal controls) of, both of these pathological processes.

Thus, it may be beneficial to provide non-invasive systems, methods and computer-accessible mediums that can differentiate between the two processes, and can quantify the degree of either pathological processes. Such systems, methods and computer-accessible mediums would be of significant clinical value for myelin related disorders (e.g., multiple sclerosis, leukodystrophy etc.) neurodegenerative disorders (e.g., Alzheimer's disease, Parkinson's disease, Huntington's disease, amyotrophic lateral sclerosis, traumatic etc.), as well as for neuropsychiatric disorders (e.g. schizophrenia), neurodevelopmental disorders (e.g. autism, attention deficit hyperactivity disorder) and other disorders. Such exemplary systems, methods and computer-accessible medium could be valuable both for diagnostic purposes (e.g., for early detection), as well as for quantitative assessment of the efficacy of treatment options.

SUMMARY OF EXEMPLARY EMBODIMENTS

Thus, to address at least such needs, certain exemplary embodiments of exemplary architectures, systems, apparatus, methods, and computer-readable medium can be provided for determining the axonal loss and myelin degradation for a given tortuosity and axonal water fraction.

Exemplary embodiments can include receiving a first input variable based on a measure of diffusion of an axonal space or structure, receiving a second input variable based on a measure of density of axons, and applying a model to determine both axonal loss and myelin degradation, based on the inputs. Additionally, exemplary embodiments can include providing the resultant measure to a computer accessible storage medium or a display. The model can be based on axonal geometry based on parallel tubes. Also, a diameter of a portion of the tubes can be based on an anatomical structure(s) and region(s) of interest of a subject. In certain exemplary embodiments, at least one ratio can be used relating to the inner and outer diameter of at least a portion of the tubes. In other exemplary embodiments neurodegeneration can be reflected by a reduction in the number of tubes. Further, the reduction in the number of tubes can decrease the tubular density to a predetermined density. This reduction can be achieved by randomly removing tubes. In certain exemplary embodiments, neurodegeneration can be reflected by changing the ratio of the inner and outer diameter of at least a portion of the tubes.

In certain exemplary embodiments, the determination can be based on a Monte Carlo simulation in a finite time domain, the Monte Carlo simulation including an extrapolation to determine a diffusion coefficient in an infinite time limit based on $$a \frac{\ln(t)}{t}$$

functional dependence on time. In other exemplary embodiments, the functional dependence on time can be in a form of $$D_\infty + c \frac{\ln(t)}{t} \text{ or } D_\infty + c \ln\left(\frac{t}{t_0}\right) \Big/ t, t \gg t_0.$$

Another exemplary embodiment of the present disclosure can include constructing a plurality of axonal geometries, each including an area, axons within the area, a border around each axon, and a space outside the borders within the area. The constructing can include varying a density of axons and a mean diameter for each geometry. The exemplary embodiments can include determining, for each geometry, an axonal loss value and a myelin degradation myelin degradation value. The exemplary embodiment can also include constructing a grid of the determined axonal loss values and myelin degradation myelin degradation values as they relate to the diffusion coefficient and the density coefficient associated with a particular geometry for each geometry. The exemplary embodiment can also include receiving a diffusion coefficient input, receiving a density coefficient input, and applying the grid to the inputs, providing a resulting axonal loss value or myelin degradation myelin degradation value. Constructing the grid can include applying a Monte Carlo simulation to each geometry.

Another exemplary embodiment can include receiving an input including a measure of diffusion of an axonal space and including a measure of density of axons within the axonal space, and applying a model to the input to produce both an axonal loss value and a myelin degradation myelin degradation value. That model can include a contour grid constructed by Monte Carlo simulations of a plurality of varying axonal geometries. The model can also be one or more analytical relations, equations or formulas.

Another exemplary embodiment can include systems, methods and computer-accessible mediums for determining axonal loss or myelin degradation myelin degradation including receiving data based a measure of diffusion of an axonal space or a measure of a density of axons and, with a hardware processor arrangement, determining axonal loss or myelin degradation myelin degradation based on the data.

Another exemplary embodiment can include systems, methods and computer-accessible mediums for determining a biomarker(s) of structural heterogeneity or structural randomness of brain tissue including receiving a dependent measure(s) of a diffusion coefficient of the brain tissue, and determining the biomarker(s) from a ln(t)/t dependence of the diffusion coefficient on diffusion time or from a linear dependence of the diffusion coefficient on diffusion frequency. In certain exemplary embodiments, a pulse-gradient spin echo technique or an oscillating gradient spin echo technique is used with nuclear magnetic resonance or magnetic resonance imaging to obtain the dependent measure(s) of the diffusion coefficient of the brain tissue. The determination is made via a fit, and the brain tissue is at least one of white matter or grey matter.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTIONS OF THE DRAWINGS

Further objects, features and advantages of the present disclosure will become apparent from the following detailed description taken in conjunction with the accompanying Figures showing illustrative embodiments of the present disclosure, in which.

Figure 1:
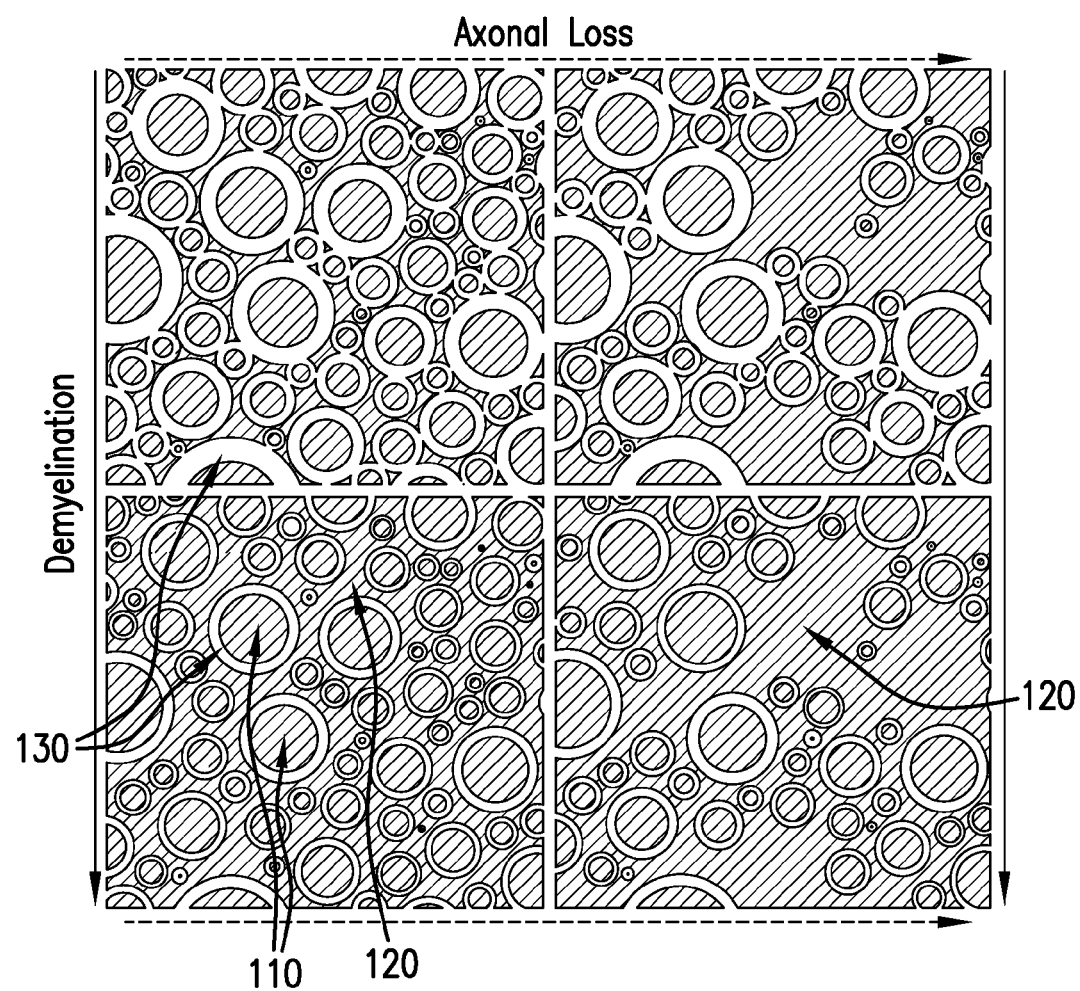
FIG. 1 illustrates exemplary variations of an exemplary axonal geometry according to certain exemplary embodiments of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures. It is intended that changes and modifications can be made to the described exemplary embodiments without departing from the true scope and spirit of the subject disclosure as defined by the appended claims.

DETAILED DESCRIPTION

The exemplary embodiments of the present disclosure may be further understood with reference to the following description and the related appended drawings. The exemplary embodiments of the present disclosure relate generally to exemplary systems, methods and computer-accessible mediums for quantifying a degree of axonal loss and myelin degradation myelin degradation using (e.g., magnetic resonance imaging). The exemplary embodiments of the present disclosure can model the relevant portion (e.g., only the most relevant portion) of white matter microarchitecture. For example, FIG. 1 illustrates a representation of a cross-section of 6 µm×6 µm through the axonal geometry used for certain exemplary simulations showing the intra-axonal space (e.g., the inner circles, two of which are marked with reference 110), extra-axonal space (e.g., the area outside the circles, two spots of which are marked with reference 120) and myelin (e.g., the circular borders of the inner circles, two of which are marked with reference 130) The representation shown is in the plane transverse to axonal fiber. Exemplary embodiments of the present disclosure can model neurodegeneration by increasing axonal loss (left to right), and/or myelin degradation myelin degradation (top to bottom). The exemplary modeling framework can quantitatively relate the two parameters of axonal water fraction ("AWF") and the tortuosity of extra-axonal space ("EAS") to the degree of myelin degradation and of axonal loss. These two input parameters, AWF and the tortuosity of EAS, can themselves be straightforwardly determined from a diffusion measurement via, for example, diffusion-weighted nuclear magnetic resonance or diffusion-weighted magnetic resonance imaging methodologies.

Figure 2:
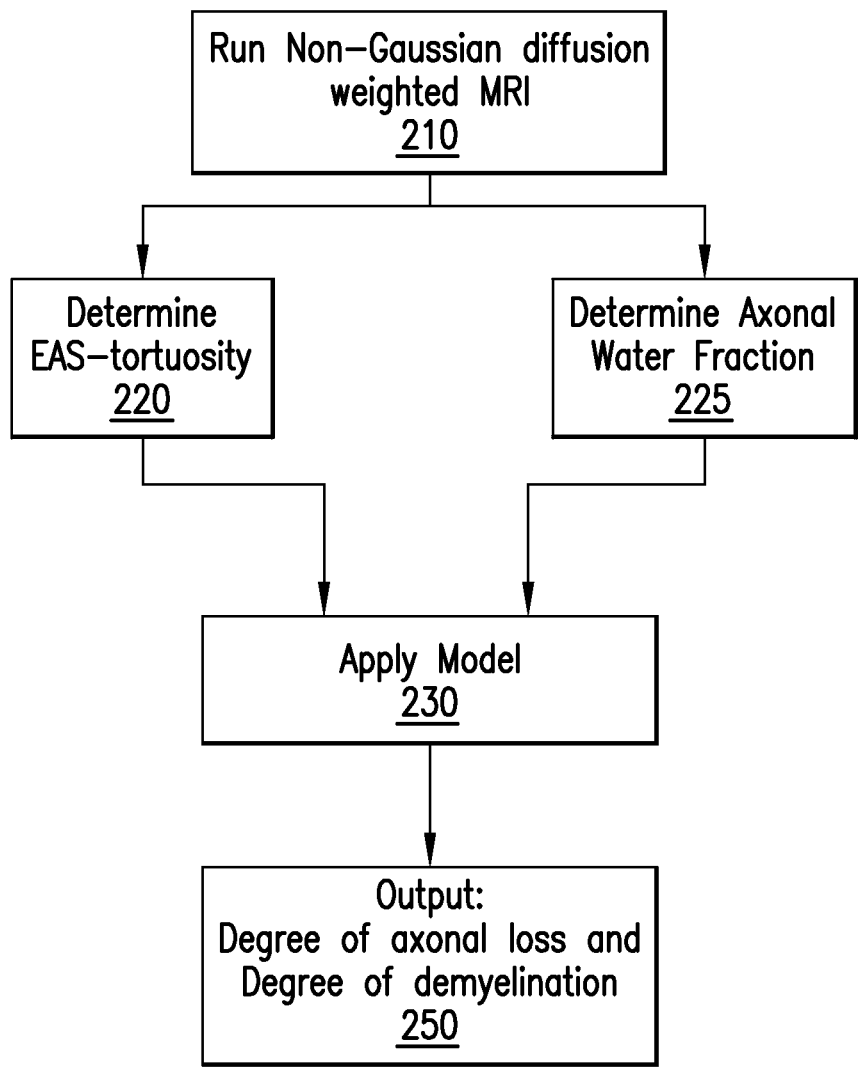
FIG. 2 illustrates a flow diagram of a method for determining the degree of axonal loss and myelin degradation myelin degradation according to certain exemplary embodiments of the present disclosure.

FIG. 2 illustrates an exemplary method for determining the degree of myelin degradation and axonal loss, according to an exemplary embodiment of the present disclosure. At procedure 210, a non-Gaussian diffusion weighted MRI can be performed. The non-Gaussian diffusion MRI can be performed in a manner that can facilitate the measurement to be sensitive to non-Gaussian diffusion effects (e.g., beyond the so-called diffusion-tensor imaging ("DTI")). DTI may only be sensitive to the combination of myelin degradation and axonal loss, but may not be specific to either of these changes, and therefore, may not be able to quantify these changes (e.g., since they have similar effects on conventional DTI metrics, such as the fractional anisotropy and radial diffusivity).

From a non-Gaussian diffusion MRI measurement data set, one can derive the two auxiliary characteristics, the EAS tortuosity (e.g., at procedure 220), and AWF (e.g., at procedure 225), using, for instance, a biexponential fit, or from a diffusional kurtosis data set. With these two inputs, a model can be generated and applied at procedure 230, specifically applied to an output (e.g., at procedure 250), as a degree of axonal loss and a degree of myelin degradation (e.g., as an indication and quantification of neurodegeneration).

The exemplary systems, methods and computer-accessible mediums can produce these outputs based on the quantitative relation between the two inputs (e.g., the EAS tortuosity and AWF), and the two outputs (e.g., the degree of axonal loss as characterized by the change in the axon density $n_a$), and the degree of myelin degradation (e.g., as characterized by the change in the so-called g-ratio between the inner and outer axonal radius), as shown in relation (1) and as described in more detail below:

$$(\text{EAS tortuosity } \Lambda, \text{ and AWF}) \Rightarrow (\text{axon density } n_a \text{ and g-ratio}) \quad (1)$$

Figure 3:
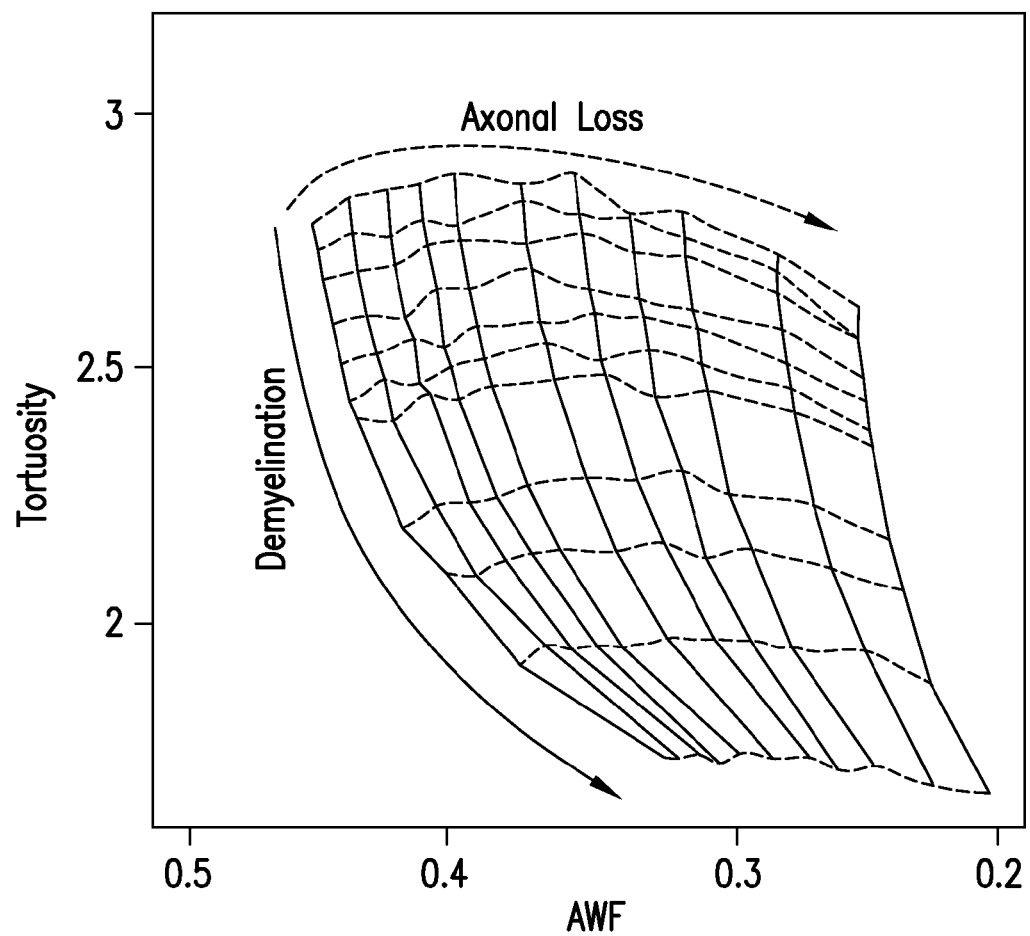
FIG. 3 is a contour grid relating tortuosity and axonal water fraction to axonal loss and myelin degradation myelin degradation according to certain exemplary embodiments of the present disclosure.

The exemplary systems, methods and computer-accessible mediums can use relation (1) in a number of different ways to produce the desired exemplary output (e.g., at procedure 250). First, an exemplary model can include a set of contour lines (e.g., as illustrated in FIG. 3), which can be calculated by means of (e.g., Monte Carlo simulations in a realistic axonal fiber geometry further described below). A second exemplary implementation can include approximate analytical expressions, described in detail below, and illustrated in FIG. 6.

FIG. 3 illustrates exemplary numerical simulations of the tortuosity as a function of the AWF for varying axon numbers and g-ratios. These results reveal that the tortuosity can decrease rapidly for increasing myelin degradation, while it is relatively unaffected by axonal loss. As illustrated in FIG. 3, the exemplary systems, methods and computer-accessible mediums can produce unexpected results, which can approximately indicate that the AWF can be most sensitive to axonal loss, while the EAS tortuosity is most sensitive to myelin degradation. However, this relation (e.g., relation (1)), as determined by the application of a model (e.g., at procedure 230), provides even greater detail than the broad sensitivity relationship. The sensitivity can be non-linear (e.g., as the contour lines in FIG. 3 illustrate). For instance, the tortuosity can actually increase initially when taking out fibers randomly (e.g., axonal loss), which can be explained qualitatively by the creation of lakes in which spins get locally trapped. Also, the AWF can decrease rapidly with axonal loss, but relatively slowly with myelin degradation. The fact that the exemplary contour lines in FIG. 3 are approximately orthogonal to each other can indicate that the inputs provide independent information, and thereby can be used to determine the output.

Relation (1), in general, depends on the axonal packing, and can be generalized onto any distribution of axonal sizes in a white matter ("WM") fiber. The exemplary systems, methods and computer-accessible mediums can obtain the specifics of relation (1) (e.g., as illustrated in FIG. 3) using realistic axonal geometry representations (e.g., as illustrated in FIG. 1), which can correspond to experimentally measured distributions of axonal sizes.

Figure 4:
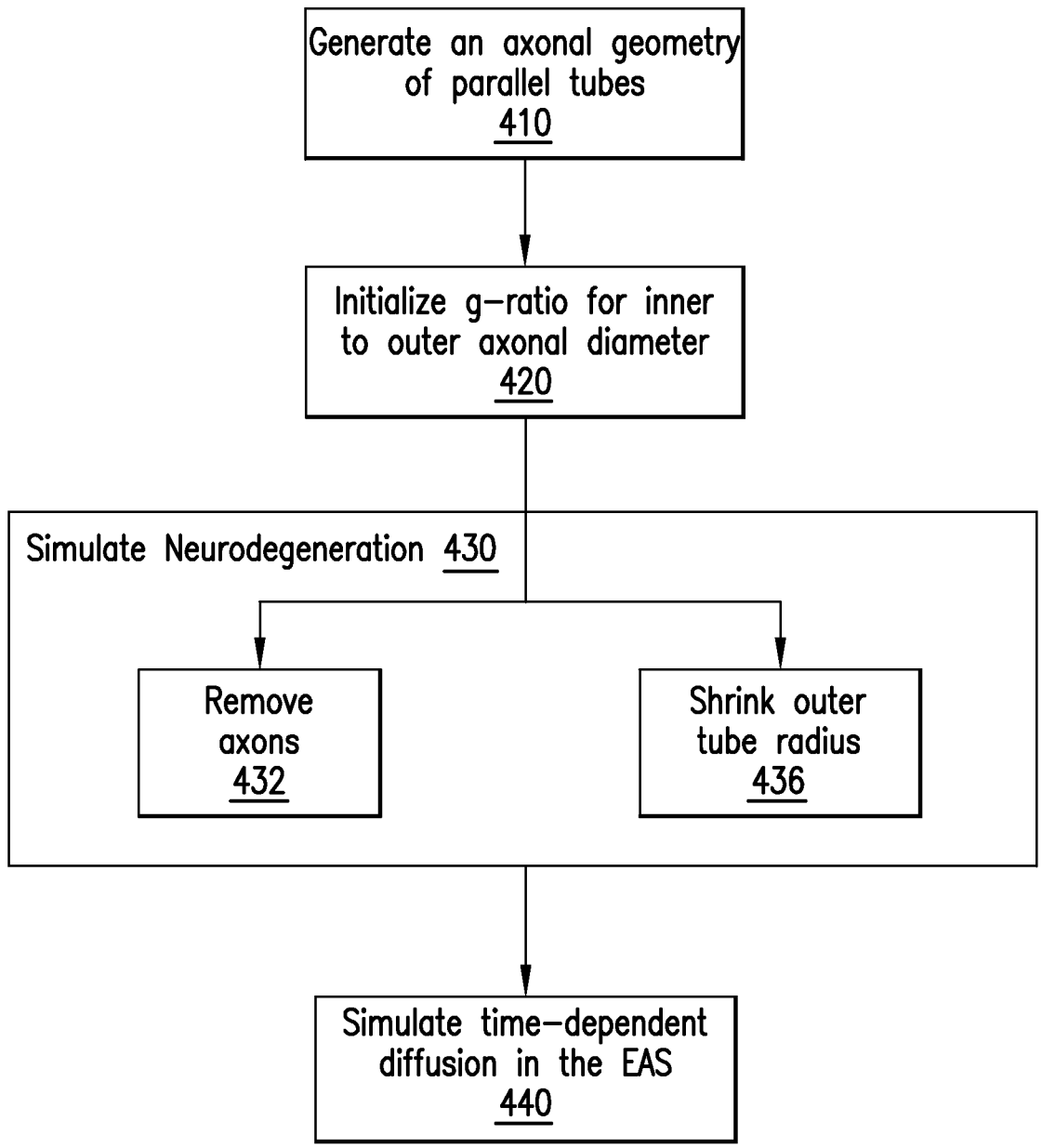
FIG. 4 is a flow diagram of a method for simulating time dependent diffusion in extra-axonal space according to exemplary embodiments of the present disclosure.

FIG. 4 illustrates an exemplary method for determining the specifics of relation (1) (e.g., the contour grid of FIG. 2 using Monte Carlo simulations). First, at procedure 410, the axons can be represented by an axonal geometry of parallel tubes with a particular mean diameter (e.g., 1 μm) and a particular diameter distribution (e.g., similar to the human corpus callosum illustrated in FIG. 5, which illustrates an exemplary histogram of the outer axon radius values used for simulating the diffusion in the extra-axonal space of the corpus callosum, mimicking the measured distribution). The radius probability density can be modeled by a gamma distribution (with $\alpha=3$ and $\beta=0.43$).

At procedure 420, the g-ratio of the inner to the outer axonal diameter (including the myelin sheath) can be initialized (e.g. at g=0.5). Neurodegeneration can then be modeled at procedure 430, which can include a number of operations or combination of operations. For example, axons can be removed (e.g., randomly) to simulate axonal loss at procedure 432, which can decrease the axonal density (e.g., from 0.44 axons/μm² to 0.27 axons/μm²). Additionally or alternatively, the outer tube radius of the axons can be uniformly shrunk to simulate myelin degradation at procedure 436 (e.g., by increasing the g-ratio from, e.g., 0.5 to 0.7). The AWF can be defined as the ratio between the intra-axonal volume 110 and the sum of the intra-axonal volume and the volume of EAS 120. The time-dependent diffusion in the EAS can be simulated at procedure 440 for each geometry (e.g., in C++ based on the dynamics of random walkers). An exemplary tortuosity $\Lambda=D_0/D_{e,\perp}$ can be defined as the ratio of the free diffusivity $D_0$ (e.g., 2 μm²/ms) over the diffusivity perpendicular to the axons, $D_{e,\perp}$, (e.g., taken at 50 ms, or extrapolated to its t->∞ limit by virtue of equation (3) described below).

While the exemplary systems, methods and computer-accessible mediums have been described with various exemplary values, applications, and other details, any number of other parameters can be used. For example, the exemplary approach can include any combination of simultaneous myelin degradation and loss of axons, and can be modified to include different ways of myelin degradation and axonal loss specific to particular diseases and brain WM regions. For example, axons can be shrunk (e.g., demyelinated) non-uniformly, or removed preferentially depending on their size, thereby changing their size distribution in the disease process.

Once the contour grid (e.g., shown in FIG. 3) is determined, the exemplary method of FIG. 2 can receive inputs (e.g., tortuosity and AWF) from (e.g., a clinical scan of a particular patient), apply the inputs to the model, and receive an associated axonal loss and myelin degradation output.

Another exemplary implementation of an exemplary embodiment according to the present disclosure can include an analytical method. The exemplary analytical method can include the following exemplary parameters: φ, can be an extra-axonal volume fraction (e.g., fraction of space not occupied by axons); $\psi$ can be the axonal volume fraction (e.g., fraction of space occupied by axons, including the myelin sheath), such that $\phi+\psi=1$; $\phi_{in}$ can be the intra-axonal volume fraction (e.g., the fraction of space inside the axons, not including the myelin sheath), e.g. $\phi_{in}=g^2\psi$; and $n_a$ can be the axon number density (e.g., the number of axons per unit cross-sectional area in a WM fiber bundle), which can be related to $\psi$ by $\psi=n_a s_a$, where $s_a$ can be the mean cross-sectional area of an axon within the fiber bundle.

In terms of these exemplary parameters, the axonal water fraction can be $$AWF = \frac{\varphi_{in}}{\varphi + \varphi_{in}}.$$

Excluding $\phi_{in}$ can yield the relation of AWF to extra-axonal volume fraction $\phi$ and the myelin g-ratio can be, for example, $$\varphi = \frac{1-AWF}{1+AWF\left(\frac{1}{g^2}-1\right)}.$$

The relation (1) used in the exemplary systems, methods and computer-accessible mediums can connect AWF and EAS tortuosity $\Lambda$ to $\psi$ and g. The exemplary systems, methods and computer-accessible mediums can derive the analytical relation $\Lambda=\Lambda(AWF, \phi, g)$. This relation (illustrated in FIG. 6), together with the formulas above, can be used to express $(\psi, g)$ via $(\Lambda, AWF)$, thereby establishing relation (1).

Figure 6:
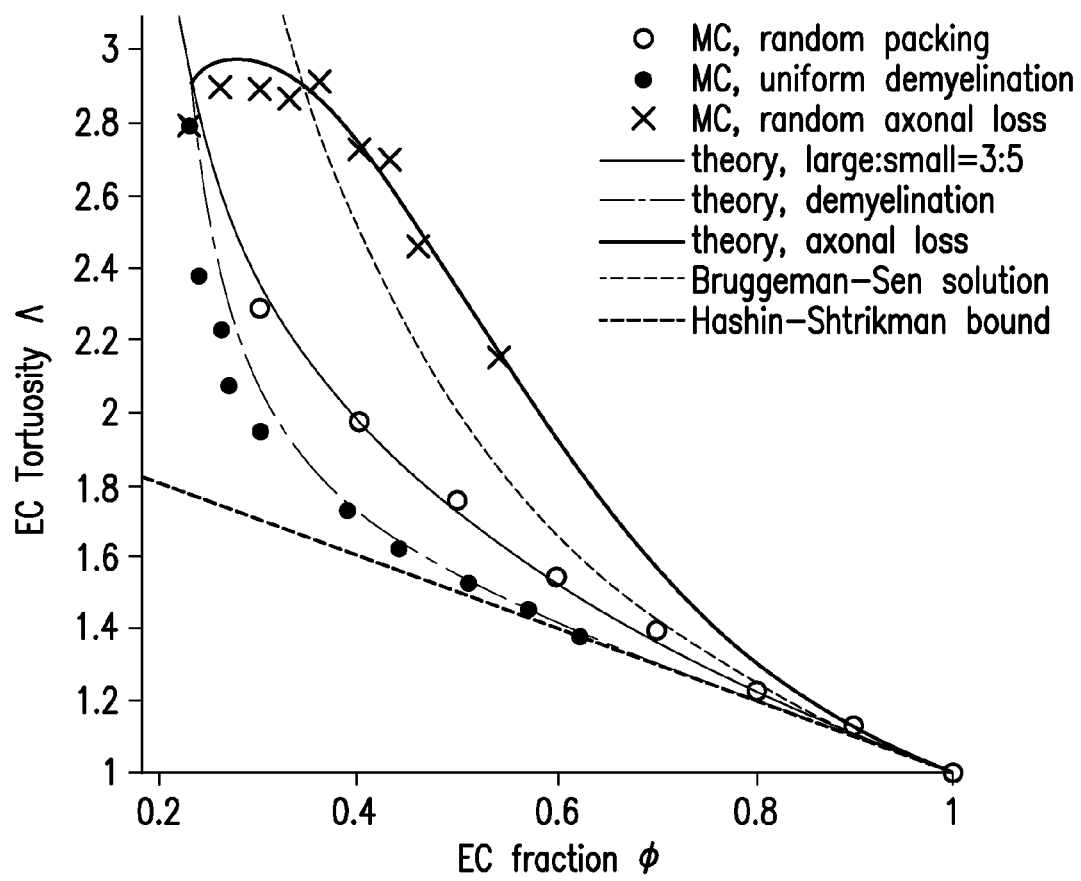
FIG. 6 is a comparison of different exemplary configurations according to exemplary embodiments of the present disclosure.

The exemplary analytical method can display quantitative agreement with the exemplary use of Monte Carlo simulations of the two-dimensional diffusion restricted by randomly packed impermeable disks whose size distribution can reflect the measured axonal diameter distribution, as described above. In the exemplary systems, methods and computer-accessible mediums, axons can be modeled as parallel impermeable cylinders (e.g., disks in the plane transverse to fiber as seen in FIG. 1) their packing affected by either axonal loss (e.g., removal of the disks), or myelin degradation (e.g., disk shrinkage). FIG. 6 shows the Monte Carlo-simulated tortuosity $\Lambda=D_0/D_e,\perp$, with $D_0$ which can be the free water diffusivity, together with results of the exemplary analytical modeling.

The exemplary systems, methods and computer-accessible mediums can account for the distribution of axon sizes. As the axonal size distribution can have both a peak (e.g., representing many small similar-size axons) and a long tail (e.g., a few large axons), the exemplary systems, methods and computer-accessible mediums can approximate the disk size distribution by two populations: "small", 's' (of the same size), and "large", 'l', with the ratio $\xi=\psi_l/\psi_s$ between their volume fractions, which can be the only adjustable parameter characterizing the distribution.

The exemplary systems, methods and computer-accessible mediums can first consider the effect of small disks, "homogenizing" at the scale exceeding their size, and then use the reduced diffusivity of population 'l' to describe the further restriction to diffusion caused by rare large disks. In this manner, the "small parameter" for the large disks can become their relative small fraction $\psi_l$. The restriction caused by tightly packed small disks can then be modeled.

However, the effect of small disks randomly placed in-between the large ones can be captured locally by the solution for a square lattice of disks. The exemplary systems, methods and computer-accessible mediums can focus on the EAS conductivity $\sigma(p)$ assuming the EAS space is filled with material with a unit conductivity $\sigma_0\equiv1$. In terms of the conductivity, the EAS tortuosity $\Lambda$ can equal $D_0/D_e,\perp=\phi/\sigma(\phi)$. The exemplary openings between small disks can form a "resistor network," which the exemplary systems, methods and computer-accessible mediums can treat locally as a square lattice made of "conductances" $\sigma_s=\sigma_\square/\psi_s(1-\psi_l)$, where $\sigma_\square(\psi)$ can be the conductivity of a square lattice of identical nonconducting disks with fraction $\psi$. Effective medium treatment of adding large disks in the background of $\sigma_s$ can yield $\sigma=\sigma_\square(\psi_s/(1-\psi_l))\cdot(1-\psi_l)^2$, (e.g., as illustrated by the curved line along the hollow-dots in FIG. 6), where "theory, large:small=3:5". Applying this exemplary two-stage approach, the tortuosity can be substantially more similar to the Monte Carlo results (e.g., open circles) than that of earlier approaches given by $\sigma=\phi^2$ and $\Lambda=1/\phi$ (e.g., as illustrated by the higher dashed line "Bruggeman-Sen solution"). In FIG. 6, the exemplary systems, methods and computer-accessible mediums can set $\xi=3:5=0.6$. This can correspond to large axons with radius exceeding ~1 μm, (see FIG. 5), contributing $\psi_l/\psi=\xi/(1+\xi)\approx38\%$ of the net axonal volume $\psi=\psi_s+\psi_l=1-\phi$.

When simulating myelin degradation in the exemplary systems, methods and computer-accessible mediums, both types of axons can be shrunk (e.g., by shrinking all disks by a common factor $\lambda>1$). The conductivity of population 'l' can become $\sigma_s\to\sigma_\square(\psi_s/\lambda^2(1-\psi_l))$. The large disks can now be substituted by disks with an impermeable core of radius $R/\lambda$, coated by a shell between $R/\lambda$ and R with free conductivity $\sigma_0$. Each such disk can be equivalent to one with conductivity $\sigma_l=\sigma_0\cdot(\lambda^2-1)/(\lambda^2+1)$; filling in the space with these disks up to the volume fraction $\psi_l$ using the exemplary approach, the solid line in FIG. 6 that traces the star dots (e.g., with no extra free parameters and $\xi$ fixed to 0.6).

Figure 5:
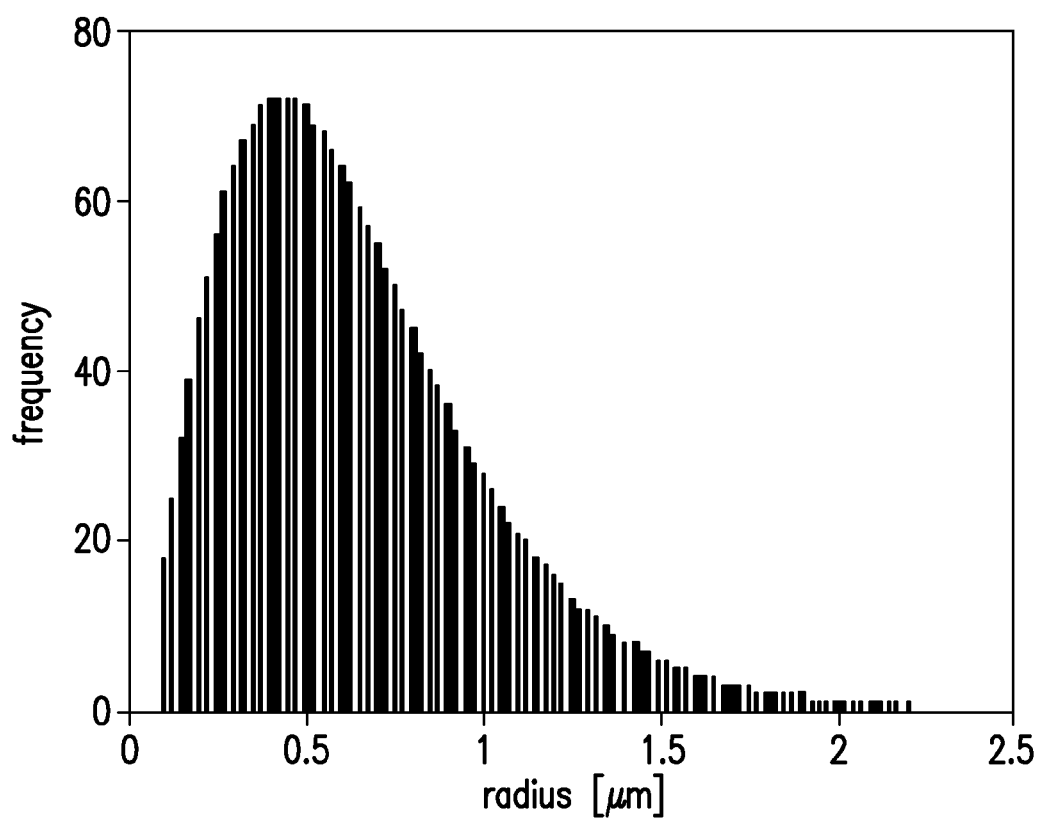
FIG. 5 is an exemplary histogram of outer axon radius values used for simulating diffusion in an extra-axonal space according to further exemplary embodiments of the present disclosure.

When simulating axonal loss in the exemplary systems, methods and computer-accessible mediums, the exemplary disks can be removed (e.g., at random irrespective of their radius), preserving the shape of their size distribution (see FIG. 5). The axonal loss can reduce the relative fraction $f_s=\psi_s/\psi_{s,0}$ of small disks (where $\psi_{s,0}$ and $\psi_{l,0}$ can be disk fractions before removal), and can be treated as the substitution of randomly chosen orthogonal bonds of a square lattice by those with unit conductance, $\sigma_\square\to\sigma_0$, increasing $\sigma_s\to\sigma_s(f_s)$. The loss of large disks can be treated using the infinitesimal addition approach, by infinitesimally increasing the fractions $f_0$ and $f_l$ of "holes" (filled with $\sigma_0$) and grains (with $\sigma_l=0$), from 0 up to $\psi_{l,0}-\psi_l$ and $\psi_l$ correspondingly, with fixed ratio $df_0/df_l$, in the background of $\sigma_s(f_s)$. The corresponding differential equation can yield an implicit solution for $\sigma(\phi)$, $\phi=1-\psi_s-\psi_l$:

$$\left(\frac{\sigma}{\sigma_s(f_s)}\right)^{\eta/2}\left(\frac{\eta\sigma+1}{\eta\sigma_s(f_s)+1}\right)^{(1-\eta)/2} = 1-\psi_{l0}, \quad (2)$$

$$\eta = \frac{f_l+f_0}{f_l-f_0} = \frac{\psi_{l0}}{2\psi_l-\psi_{l0}},$$

This is illustrated in FIG. 6, with the line "theory, axonal loss" that can trace the "X" marks (e.g., corresponding to Monte Carlo simulations), again it can have no extra free parameters (keeping the same $\xi=0.6$).

The exemplary systems, methods and computer-accessible mediums, having a strong agreement between the analytical method and Monte Carlo simulations, even for very tight packings, can suggest that the most relevant feature of the axonal size distribution can be the relative contribution $\xi$ of its tail (e.g., large axons) to its bulk (e.g., small axons), with the variation of sizes within those populations being less important. This approach can also explain the approximate decoupling of axonal loss and myelin degradation in the EAS diffusion determined in the numerical simulations discussed above. While myelin degradation can sharply increase the "conductance" of the tightly packed population 's', leading to a sharp tortuosity drop, the axonal loss can introduce isolated conducting "pockets" in the midst of poorly conducting bulk, resulting in a very slow initial conductivity increase, and can result in the initial overall decrease of EAS diffusivity $D_e \propto \sigma(\phi)/\phi$ in response to the increase of $\phi$ (FIG. 6). This approximate decoupling of axonal loss and myelin degradation, together with a theoretical framework able to capture the nonlinear relation (1), can facilitate one to differentiate between different kinds of WM damage, and to quantify their relative contributions to neurodegeneration. The exemplary approach can be utilized onto the simultaneous myelin degradation and loss of small and/or large axons, and can be straightforwardly modified to include different ways of myelin degradation and axonal loss specific to particular diseases and brain WM regions; for example, when axons are shrunk (e.g., demyelinated) non-uniformly, or removed preferentially depending on their size.

It should be noted that FIG. 1 illustrates one exemplary illustration of an axonal cross-section, illustrating axonal loss left to right, and myelin degradation top to bottom. These figures, along with the above described variations (e.g., random axon removal and/or diameter shrinking), are only one exemplary configuration, which can be used to build exemplary models of general cases. However, other configurations are also possible, such as by adding more parameters or shapes, etc. Certain modifications to these model building variations could correlate to known parameters. For example, if it is known that certain characteristics of a patient mean their actual axonal geometry is more oval than round, models can be built for those tailored cases. This can lead to even better output results for cases with known specific characteristics, but can also lead to lower accuracy results if applied to people without the specific trait, and thus may not improve the generalized model. Certain characteristics, as they become known, may refine the generalized and/or any number of specialized models, and can also provide exemplary embodiments.

Figure 7:
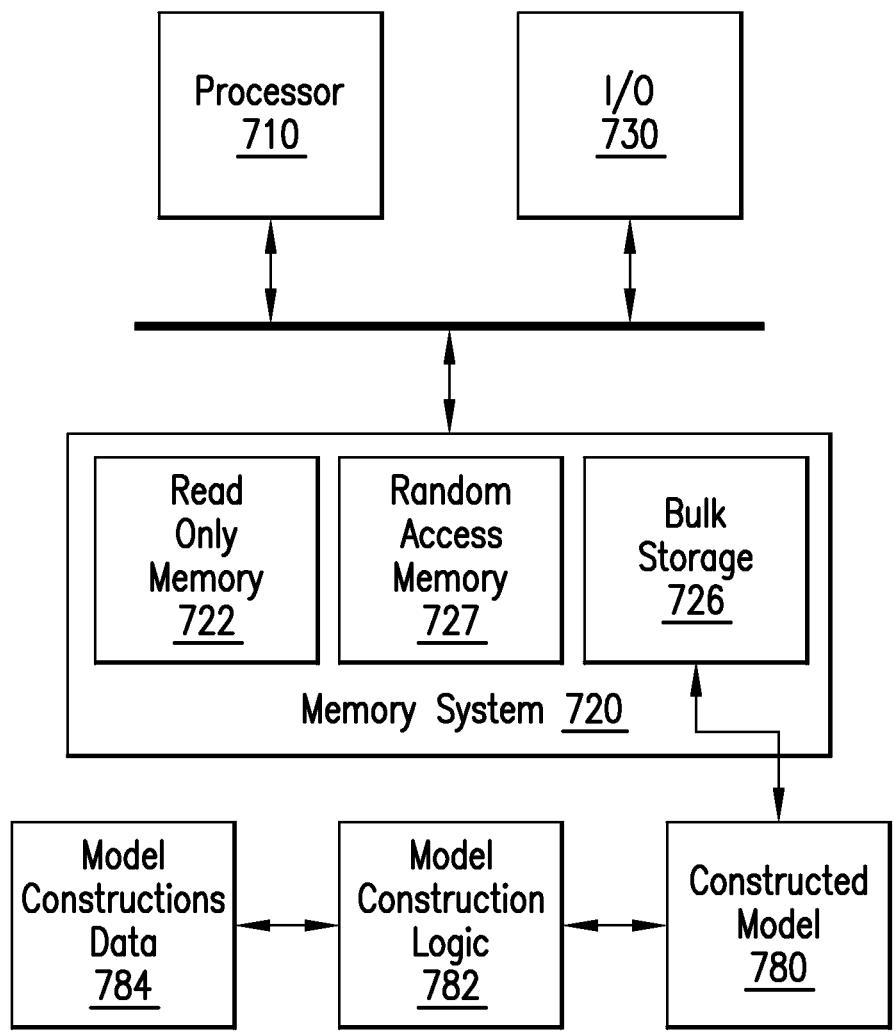
FIG. 7 is a system diagram according to further exemplary embodiments of the present disclosure.

FIG. 7 illustrates an exemplary system 700 configured to execute exemplary procedures, according to other exemplary embodiments of the present disclosure. The exemplary system 700 can include a processor 710, an input/output port 730, and various memories 720, including e.g., read only memory 722, random access memory 727, and bulk storage memory 726 (e.g., a disk drive, network drive, database, etc.) Model construction data 784 can be stored in memory, such as axonal geometries (e.g., as illustrated in FIG. 1). Model constructions logic 782 can be stored in memory, e.g., as described in other exemplary embodiments. Additionally, one or more constructed models 780 can be stored in memory (e.g., the contour grid illustrated in FIG. 2, or the analytical formulas described above).

Randomness in exemplary fiber arrangements, in a bundle, can cause the diffusion coefficient transverse to fibers D(t) to depend on diffusion time, with the exemplary quantity used above, $D_e, \perp = D_\infty$, which can be its infinite-time limit. In particular, this time dependence can have a logarithmic singularity at long diffusion times, which can be modeled as:

$$D(t) \equiv \left\langle \frac{x^2}{2t} \right\rangle \cong D_\infty + c \ln\left(\frac{t}{t_0}\right) \Big/ t, \, t \gg t_0 \quad (3)$$

This singularity can be a consequence of short-range disorder in the fiber packing. As axons are ~1 μm in diameter, almost any measurement can be in the long-time limit. Therefore, the above exemplary singularity can significantly affect the interpretation of time dependent diffusion-based methods for evaluating fiber integrity. The power law exponent θ describing the approach of the tortuosity limit $D_\infty$ can yield information about the type of disorder in a system. This exponent can appear both in the instantaneous diffusion coefficient $D_{inst}(t)$, and in oscillating gradient spin echo ("OGSE")D(ω). An example of $D_{inst}(t)$ can be:

$$D_{inst}(t) \equiv \frac{1}{2} \frac{\partial}{\partial t} \langle x^2 \rangle = D_\infty + at^{-\theta} + \ldots \Leftrightarrow D(\omega) = D_\infty + b|\omega|^\theta + \ldots \quad (4)$$

In two dimensions, θ=1 for the most commonplace random packing characterized by short-ranged disorder in fiber placement. The integration of $D_{inst}(t)$ up to t and dividing by t can yield the ln t/t behavior of D(t) in Eq. (3) above. Conversely, for any more ordered arrangement (e.g. periodic), θ>1, which can yield D(t)~$D_\infty$+c/t. Therefore, in a D(t) measurement, the effect of disorder can be in the extra ln t factor.

The coefficients a, b, and c in above equations can serve as the metric of the amount of structural disorder (e.g., randomness) in the axonal packing in a fiber bundle. They can also serve as biomarkers of disease progression tied to the miscrostructural changes in white matter fiber bundle integrity.

Exemplary Illustrations from Monte Carlo Simulations

Figure 10A:
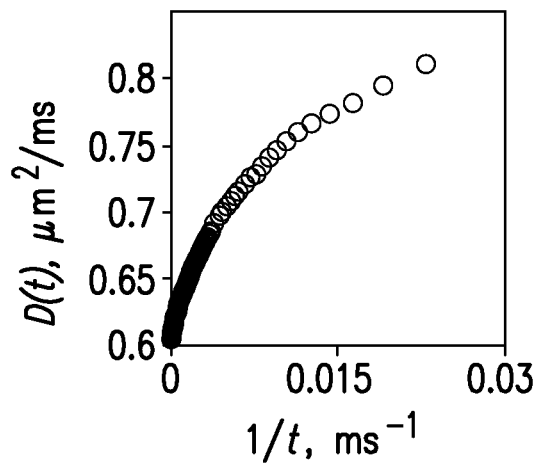
FIG. 10A illustrates an exemplary graph using Monte Carlo simulated data according to certain exemplary embodiments of the present disclosure.
Figure 10B:
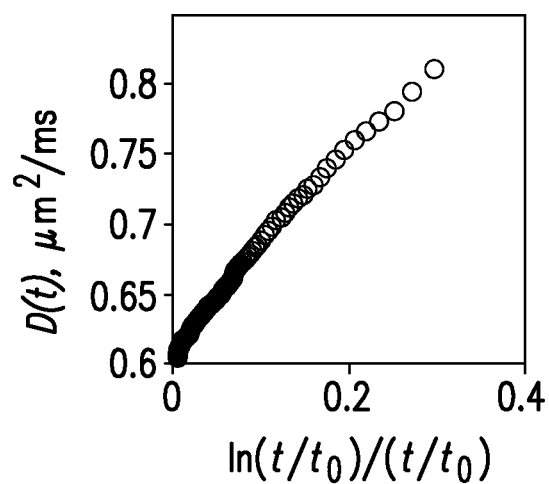
FIG. 10B illustrates a further exemplary graph using Monte Carlo simulated data according to certain exemplary embodiments of the present disclosure.

FIGS. 10A-B illustrate D(t) data plotted with respect to 1/t and $\ln(t/t_0)/(t/t_0)$, respectively. In FIG. 10A, a slight curve can be seen in the data which can indicate the logarithmic singularity. FIG. 10 shows that the bend can be removed when plotted with respect to $\ln(t/t_0)/(t/t_0)$, with a particular fitted value of $t_0$=7.3 ms (depending on the fiber size distribution).

Exemplary Implication for Pulse-Gradient Spin Echo Technique

The diffusion restricted inside axons, giving the 1/t contribution, can be used to probe the internal diameter distribution. However, t-dependence in the extra-axonal space can be more relevant, as ln(t)/t eventually exceeds 1/t in long-t limit. Therefore, modeling the disorder in extra-axonal space can be important for interpreting such measurements.

Exemplary Implication for Oscillating Gradient Spin Echo Technique

The non-analytic ln(t)/t in D(t) can translate into linear behavior in |ω| (a sharp kink in D(ω) for near ω=0). Such sharp, non-parabolic, behavior can indicate 2-dimensional disorder inextracellular space. For ordered arrangements, or for confined diffusion (e.g. inside axons), the 1/t behavior in D(t) can translate into $\omega^2$ in D(ω). This parabolic behavior can be less relevant than |ω| at small ω and the effect of packing disorder can again dominate over that of confined water.

Exemplary Conclusion of Time-Dependent Diffusion

An exemplary logarithmic singularity in two-dimensional diffusion can be demonstrated as a hallmark of disordered packing geometries. This singularity can dominate the time-dependence of diffusion across axonal fiber bundles, and can be included in any quantification scheme for adequate fiber characterization.

Exemplary Implication for Determining the Infinite-Time (Tortuosity) Limit of Diffusion Coefficient from Finite-Time Monte Carlo Simulations When modeling diffusivity and tortuosity in the extra-axonal space (EAS), the t->∞ asymptote of the diffusion coefficient in the EAS needs to be obtained. With Monte-Carlo simulations, infinite times can never be achieved, and taking long-time limit can be computationally very costly. The above universal functional form of equation (3), of the time-dependent diffusion coefficient D(t) in a disordered two-dimensional medium, can be valid at sufficiently long times (e.g., the asymptotic regime).

Fitting the numerical (or experimental) data to the formula of equation (3) yields, in particular the t=∞ limit (the first term on the right-hand side of the above equation), which can be taken as the bulk value $D_e,\perp$ used above. This can be the needed diffusivity in the infinite-time limit. Since the way this value is being approached is fairly slow, ~(log t)/t, the above asymptotic relation can be beneficial over simulating, for example, at an extra order-of-magnitude in time on a computer, just to get closer to the true $D_e,\perp$.

The slowness of this approach can be demonstrated using the Monte Carlo simulations in FIG. 10. In FIG. 10B, the same Monte Carlo MC data can be plotted as function of $\ln(t/t_0)/t$, with a particular value of $t_0$ obtained from a fit to equation (3). As a function of $x=\ln(t/t_0)/t$, the diffusion coefficient can become a linear function of x. This can facilitate the ability to go to the t=∞ limit by simply interpolating to x=0, where this line intersects the y-axis.

Exemplary Clinical Application

Figure 9A:
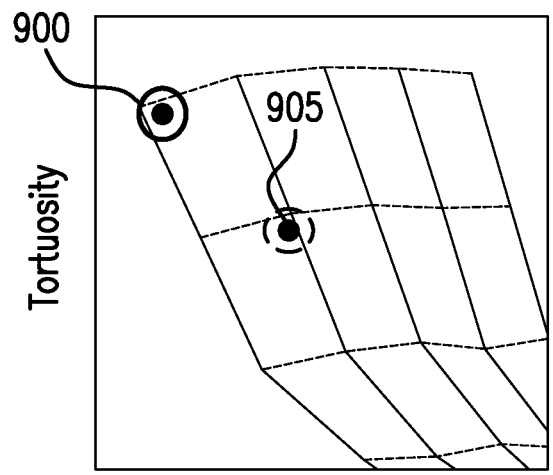
FIG. 9A is an exemplary graph of an exemplary clinical study of patients with relapsing remitting multiple sclerosis according to certain exemplary embodiments of the present disclosure.
Figure 9B:
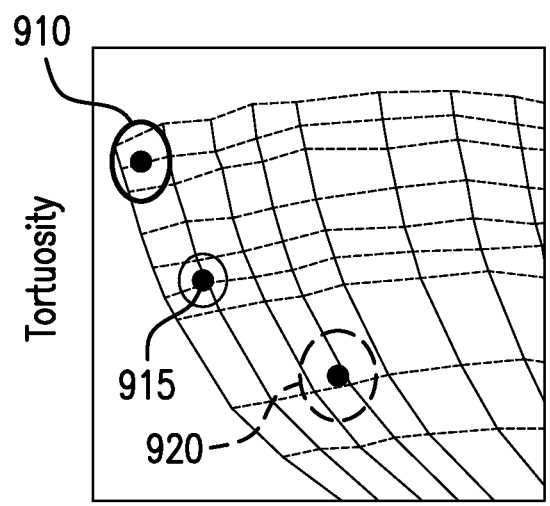
FIG. 9B is an exemplary graph of an exemplary clinical study of patients with Alzheimer's disease and subjects with mild cognitive impairment according to certain exemplary embodiments of the present disclosure.

FIGS. 9A-B illustrate data from clinical studies that can be selected graphing tortuosity and AWF for comparison with the numerical simulations. The first exemplary study of relapsing remitting multiple sclerosis included 51 young subjects consisting of (1) 32 patients with relapsing remitting multiple sclerosis having a mean age of 29±9 years, a mean disease duration of 3.6±4.0 and a median expanded disability status scale 2.0 (element 905 of FIG. 9A) and (2) 19 patients that matched normal controls having a mean age of 36±11.4 years (element 900 of FIG. 9A). The second exemplary study of Alzheimer's disease included 42 elderly subjects consisting of (1) 15 patients with normal control having a mean age of 76±4.3 years (element 910 of FIG. 9B), (2) 12 subjects with mild cognitive impairment having a mean age of 79.2±7.3 years (element 915 of FIG. 9B) and (3) 15 patients with probable Alzheimer's disease having a mean age of 78.3±9.6 years (element 920 of FIG. 9B). Diffusion imaging was performed with 3 b-values (0, 1000 and 2000 s/mm$^2$) along 30 diffusion encoding directions. WM parametric maps were derived yielding maps for the AWF and tortuosity. The multiple sclerosis analysis is restricted to normal appearing WM by removing all voxels in lesions. All parametric maps were transformed to a standard space using TBSS8 and average values of the AWF and tortuosity in the corpus callosum genu and splenium were derived based on the John Hopkins University WM label atlas for group comparisons.

Exemplary Results

Numerical simulations of the tortuosity as a function of the AWF (FIG. 3) for varying axon number and g-ratio, revealed that the tortuosity can decrease rapidly for increasing myelin degradation, while it can be relatively unaffected by axonal loss. The tortuosity can even increase initially when removing fibers randomly, which can be explained qualitatively by the creation of lakes in which spins get locally trapped. The AWF can decrease rapidly with axonal loss, but can decrease relatively slowly with myelin degradation. Therefore, the AWF and tortuosity can be used to distinguish between axonal loss and myelin degradation, demonstrating the advantage of non-Gaussian diffusion metrics. The distinction between axonal loss and myelin degradation is illustrated in FIG. 3 for the genu in multiple sclerosis patients compared to age-matched normal controls, and for the splenium in Alzheimer's disease patients compared to mild cognitive impairment subjects and aged matched normal controls. A strong dependence of the AWF and tortuosity with age can be observed, and the tortuosity and AWF are consistently higher in the splenium than in the genu, which is explained by the varying degree of myelination and axonal density across the corpus callosum. The change between the young normal control and multiple sclerosis in both the AWF and tortuosity (left side of FIG. 3) can indicate that relapsing remitting multiple sclerosis pathology can be characterized by both axonal loss and myelin degradation, which agrees with postmortem histological studies. The change between elderly normal control and mild cognitive impairment (right side of FIG. 3) can be larger in the tortuosity than in the AWF, suggestive of myelin degradation, while the change between mild cognitive impairment and Alzheimer's Disease can be larger in the AWF than in tortuosity, suggestive of axonal loss as the more important neurodegenerative process for conversion from mild cognitive impairment to Alzheimer's Disease. The exemplary systems, methods and computer-accessible mediums can provide an MRI-measured EAS tortuosity and AWF, and can provide new biomarkers for myelin degradation and axonal loss respectively.

Figure 8:
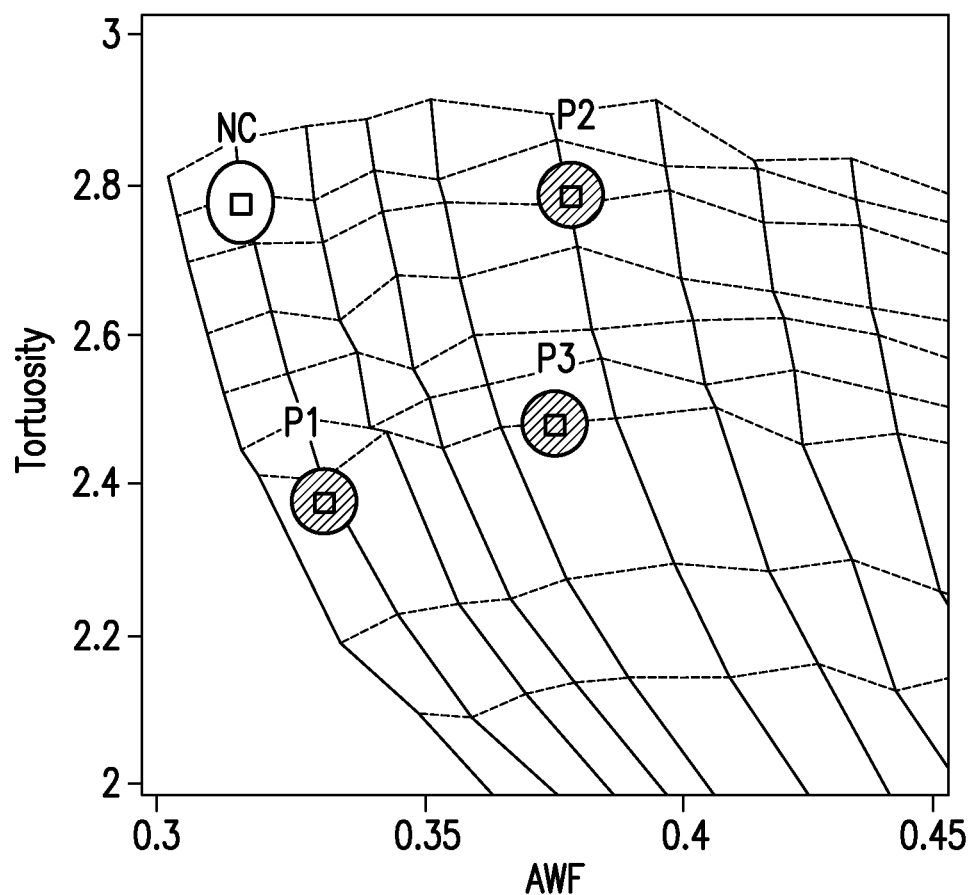
FIG. 8 is a data point comparison overlay of the contour grid illustrated in FIG. 3, according to further exemplary embodiments of the present disclosure.

The exemplary systems, methods and computer-accessible mediums described herein can be used to quantify the axonal loss and myelin degradation in a plethora of neurodegenerative diseases (e.g., Alzheimer's disease, Parkinson's disease, Huntington's disease, amyotrophic lateral sclerosis, traumatic brain injury and multiple sclerosis). Using non-Gaussian diffusion MRI methods in patients with a given white matter pathology, the exemplary systems, methods and computer-accessible mediums can measure the axonal water fraction and tortuosity in a given white matter region consisting of sufficiently aligned axons (e.g., the WM tract in genu or splenium of the corpus callosum), and then compare those measured values with the corresponding values in the same white matter region of healthy age matched controls. Alternatively or additionally, the white matter skeleton (based on fractional anisotropy maps) can also be used, and voxelwise comparison can be performed along the skeleton between patients and age matched normal controls, or can be compared to the values along specific fiber tracts using fiber tractography. The exemplary systems, methods and computer-accessible mediums can then be used to derive the degree of myelin degradation and axonal loss for the patient, relative to the age-matched normal controls (e.g., referring to a separately built database). This principle can be illustrated by FIG. 8, where the average values for the tortuosity and AWF in a normal age matched control, as well as for 3 patients (P1, P2, P3) with different pathologies are overlaid on the grid illustrated in FIG. 3, revealing that P1 can represent a dominantly demyelinating pathology, while P2 can be characterized by mainly axonal loss and P3 can be combination of both myelin degradation and axonal loss.

Other applications can include quantifying the changes in size distribution of any fibrous tissue (e.g., muscle tissue in the case of sufficiently low cell membrane permeability), as well as applications beyond biomedical MRI (e.g., quantifying the degree of shrinkage and/or loss of any granular medium in materials sciences and porous media applications) as well as used in (e.g., food characterization or porous rock characterization with diffusion nuclear magnetic resonance (NMR")/MRI). These applications can require the extension of the exemplary systems, methods and computer-accessible mediums onto three-dimensional packings. Furthermore, using the equivalence between diffusion, electrical conduction, heat conduction, dielectric function, and magnetic permittivity, the exemplary systems, methods and computer-accessible mediums can be straightforwardly modified to apply in quantifying the changes in transport, dielectric or magnetic properties of granular and or composite media.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.
1 Bjartmar C et al. *Neurol.* 57 1248 (2001).
2 Evangelou N et al. *Ann. Neurol.* 47 391 (2000).
3 Evangelou N et al. *Brain* 124 1813 (2001).
4 Brun A & Englund E *Ann Neurol.* 19 253 (1986).
5 Fieremans E et al. *NMR Biomed* 23 711 (2010).
6 Fieremans E et al. *Neuroimage* 58 177 (2011).
7 Aboitiz F et al. *Brain Res.* 598 143 (1992).
8 O F Mossotti, *Mem. di mathem. e fisica in Modena* 24 11 (1850) 49.
9 J C Maxwell, *A Treatise on Electricity and Magnetism* (Clarendon, 1892).
10 J C M Garnett, *Phil Trans R Soc Lond*, B203 (1904) 385
11 R Landauer, *AIP Conf Proc* 40 (1978) 2.
12 D A G Bruggeman, *Ann Phys (Leipzig)* 24 (1935) 636.
13 P N Sen et al, *Geophysics* 46 (1981) 781.
14 L L Latour et al, *PNAS* 91 (1994) 1229.
15 D S Novikov & V G Kiselev, *NMR Biomed* 23 (2010) 682.
16 Z Hashin & S Shtrikman, *J Appl Phys* 33 (1962) 3125.
17 W T Perrins et al, *Proc R Soc Lond A*369 (1979) 207.
18 S Kirkpatrick, *Rev Mod Phys* 45 (1973) 574.
19 Barazany D et al. *Brain* 132 (2009) 1210
20 Klawiter E et al. *Neuroimage* 55 (2011) 1454
21 Smith S M et al. *Neuroimage* 31 (2006) 1487
22 Lazar M et al. *NMR Biomed* (2010) 821

The invention claimed is:

1. A non-transitory computer-accessible medium having stored thereon computer-executable instructions for determining at least one of axonal loss or myelin degradation, wherein, when a computer hardware arrangement executes the instructions, the computer arrangement is configured to perform procedures comprising:
    determining at least one of a measure of diffusion in an extra-axonal space or an axonal water fraction (AWF); and
    determining the at least one of the axonal loss or the myelin degradation based on the at least one of the measure of the diffusion in the extra-axonal space or the AWF using at least one of a nuclear magnetic resonance arrangement or a magnetic resonance imaging arrangement.

2. The non-transitory computer-accessible medium of claim 1, wherein the computer arrangement is configured to determine the at least one of the axonal loss or the myelin degradation based on axonal geometry of a plurality of parallel tubes.

3. The non-transitory computer-accessible medium of claim 2, wherein at least one diameter of at least a portion of the parallel tubes is based on at least one anatomical structure or region of interest of a subject.

4. The non-transitory computer-accessible medium of claim 2, wherein at least one ratio is used relating to the inner and outer diameter of at least a portion of the parallel tubes.

5. The non-transitory computer-accessible medium of claim 2, wherein neurodegeneration is reflected by a reduction in a number of the parallel tubes.

6. The non-transitory computer-accessible medium of claim 5, wherein the reduction in the number of the parallel tubes decreases the tubular density to a predetermined density.

7. The non-transitory computer-accessible medium of claim 5, wherein the reduction in the number of the parallel tubes is achieved by randomly removing at least one of the parallel tubes.

8. The non-transitory computer-accessible medium of claim 2, wherein neurodegeneration is reflected by changing a ratio of the inner and outer diameter of at least a portion of the parallel tubes.

9. The non-transitory computer-accessible medium of claim 2 wherein neurodegeneration is reflected by a reduction in a number of the parallel tubes, and by changing a ratio of an inner and outer diameter of at least a portion of the parallel tubes; and wherein a simulation is performed to determine the at least one of the axonal loss or the myelin degradation as a function of at least one of a tortuosity of the extra-axonal space (EAS) or the AWF relative to one or more axonal geometries.

10. The non-transitory computer-accessible medium of claim 9, wherein a resultant measure is used to characterize at least one of a tissue or a region of interest in a subject relative to a disease state.

11. The non-transitory computer-accessible medium of claim 1, wherein the computer arrangement is configured to determine the at least one of the axonal loss or the myelin degradation using a model of axonal geometry based on parallel cylinders.

12. The non-transitory computer-accessible medium of claim 11, wherein the parallel cylinders are impermeable.

13. The non-transitory computer-accessible medium of claim 12, wherein the axonal geometry is characterized by two populations.

14. The non-transitory computer-accessible medium of claim 13, wherein a ratio of volume fractions is an adjustable parameter for characterizing a distribution.

15. The non-transitory computer-accessible medium of claim 14, wherein disk geometry is used in a plane transverse to the cylinders.

16. The non-transitory computer-accessible medium of claim 1, wherein computer arrangement is further configured to determine the at least one of the axonal loss or the myelin degradation based on a Monte Carlo simulation in a finite time domain.

17. The non-transitory computer-accessible medium of claim 16, wherein the Monte Carlo simulation includes an extrapolation to determine a diffusion coefficient in an infinite time limit based on $$a\frac{\ln(t)}{t}$$

functional dependence on time.

18. The non-transitory computer-accessible medium of claim 17, wherein the functional dependence on time is in a form of at least one of $$D_\infty + c\frac{\ln(t)}{t} \text{ or } D_\infty + \frac{c\ln\left(\frac{t}{t_0}\right)}{t}, t \gg t_0.$$

19. A system for determining at least one of axonal loss or myelin degradation, comprising:
at least one computer hardware arrangement configured to:
determine at least one of a measure of diffusion in an extra-axonal space or an axonal water fraction (AWF); and
determine the at least one of the axonal loss or the myelin degradation based on the at least one of the measure of the diffusion in the extra-axonal space or the AWF using at least one of a nuclear magnetic resonance arrangement or a magnetic resonance imaging arrangement.

20. The system of claim 19, wherein the at least one computer hardware arrangement is configured to determine the at least one of the axonal loss or the myelin degradation by modeling a contour grid constructed by Monte Carlo simulations of a plurality of varying axonal geometries.

21. A method for determining at least one of axonal loss or myelin degradation comprising:
determining at least one of a measure of diffusion in an extra-axonal space or an axonal water fraction (AWF); and
with a hardware processing arrangement, determining the at least one of the axonal loss or the myelin degradation based on the at least one of the measure of the diffusion in the extra-axonal space or the AWF using at least one of a nuclear magnetic resonance arrangement or a magnetic resonance imaging arrangement.

22. A non-transitory computer-accessible medium having stored thereon computer-executable instructions for determining at least one of axonal loss or myelin degradation, wherein, when a computer hardware arrangement executes the instructions, the computer arrangement is configured to perform procedures comprising:
determining at least one of a measure of diffusion in an extra-axonal space or a measure of a density of axons;
constructing a plurality of axonal geometries by varying packing geometry of axons for each geometry, each of the plurality of axonal geometries including at least one of an area, axons within the area, a border around each axon, or a space outside the borders within the area;
determining, for each geometry, a density coefficient and a diffusion coefficient of an extra-axonal space;
constructing a grid of the determined diffusion coefficient and the density coefficient as they relate to at least one of an axonal loss value or a myelin degradation value associated with a particular geometry, for each geometry;
applying the grid to the at least one of the measure of the diffusion in an extra-axonal space or the measure of a density of axons; and
determining the at least one of the axonal loss or the myelin degradation.

23. The non-transitory computer-accessible medium of claim 22, wherein varying packing geometry includes varying at least one of (1) density, (2) size distribution, (3) a ratio between inner and outer diameter of axons, or (4) removing a set of axons from the area.

24. The non-transitory computer-accessible medium of claim 22, wherein the density coefficient is an axonal water fraction.

25. The non-transitory computer-accessible medium of claim 22, wherein the constructing of the grid includes applying a Monte Carlo simulation to each geometry.

26. A method for determining at least one of axonal loss or myelin degradation, comprising:
determining at least one of a measure of diffusion in an extra-axonal space or a measure of a density of axons;
constructing a plurality of axonal geometries by varying packing geometry of axons for each geometry, each of the plurality of axonal geometries including at least one of an area, axons within the area, a border around each axon, or a space outside the borders within the area;
determining, for each geometry, a density coefficient and a diffusion coefficient of an extra-axonal space;
constructing a grid of the determined diffusion coefficient and the density coefficient as they relate to at least one of an axonal loss value or a myelin degradation value associated with a particular geometry, for each geometry;

applying the grid to the at least one of the measure of the diffusion in an extra-axonal space or the measure of a density of axons; and using a computer hardware arrangement, determining the at least one of the axonal loss or the myelin degradation.

27. A system for determining at least one of axonal loss or myelin degradation, comprising:
a computer hardware arrangement configured
determine at least one of a measure of diffusion in an extra-axonal space or a measure of a density of axons;
construct a plurality of axonal geometries by varying packing geometry of axons for each geometry, each of the plurality of axonal geometries including at least one of an area, axons within the area, a border around each axon, or a space outside the borders within the area;
determine, for each geometry, a density coefficient and a diffusion coefficient of an extra-axonal space;
construct a grid of the determined diffusion coefficient and the density coefficient as they relate to at least one of an axonal loss value or a myelin degradation value associated with a particular geometry, for each geometry;
apply the grid to the at least one of the measure of the diffusion in an extra-axonal space or the measure of a density of axons; and
determine the at least one of the axonal loss or the myelin degradation.

28. A non-transitory computer-accessible medium having stored thereon computer-executable instructions for determining at least one of axonal loss or myelin degradation, wherein, when a computer hardware arrangement executes the instructions, the computer arrangement is configured to perform procedures comprising:
determining at least one of a measure of diffusion in an extra-axonal space or a measure of a density of axons; and
determining the at least one of the axonal loss or the myelin degradation based on the at least one of the measure of the diffusion in the extra-axonal space or the measure of the density of axons using a Monte Carlo simulation in a finite time domain, wherein the Monte Carlo simulation includes an extrapolation by the computer arrangement to determine a diffusion coefficient in an infinite time limit based on $$a \frac{\ln(t)}{t}$$

functional dependence on time.

29. A method for determining at least one of axonal loss or myelin degradation, comprising:
determining at least one of a measure of diffusion in an extra-axonal space or a measure of a density of axons; and
using a computer hardware arrangement, determining the at least one of the axonal loss or the myelin degradation based on the at least one of the measure of the diffusion in the extra-axonal space or the measure of the density of axons using a Monte Carlo simulation in a finite time domain, wherein the Monte Carlo simulation includes an extrapolation by the computer arrangement to determine a diffusion coefficient in an infinite time limit based on $$a \frac{\ln(t)}{t}$$

functional dependence on time.

30. A system for determining at least one of axonal loss or myelin degradation, comprising:
determine at least one of a measure of diffusion in an extra-axonal space or a measure of a density of axons; and
determine the at least one of the axonal loss or the myelin degradation based on the at least one of the measure of the diffusion in the extra-axonal space or the measure of the density of axons using a Monte Carlo simulation in a finite time domain, wherein the Monte Carlo simulation includes an extrapolation by the computer arrangement to determine a diffusion coefficient in an infinite time limit based on $$a \frac{\ln(t)}{t}$$

functional dependence on time.

31. A non-transitory computer-accessible medium having stored thereon computer-executable instructions for determining at least one of axonal loss or myelin degradation, wherein, when a computer hardware arrangement executes the instructions, the computer arrangement is configured to perform procedures comprising:
determining at least one of a measure of diffusion in an extra-axonal space or a measure of a density of axons; and
determining the at least one of the axonal loss or the myelin degradation using the at least one of the measure of the diffusion in the extra-axonal space or the measure of the density of axons based on axonal geometry of a plurality of parallel tubes
wherein neurodegeneration is reflected by a reduction in a number of the parallel tubes, and by changing a ratio of an inner and outer diameter of at least a portion of the parallel tubes; and
wherein a simulation is performed to determine the at least one of the axonal loss or the myelin degradation as a function of at least one of a tortuosity of the extra-axonal space (EAS) or axonal water fraction (AWF) relative to one or more axonal geometries.

32. A method for determining at least one of axonal loss or myelin degradation, comprising:
determining at least one of a measure of diffusion in an extra-axonal space or a measure of a density of axons; and
using a computer hardware arrangement, determining the at least one of the axonal loss or the myelin degradation using the at least one of the measure of the diffusion in the extra-axonal space or the measure of the density of axons based on axonal geometry of a plurality of parallel tubes
wherein neurodegeneration is reflected by a reduction in a number of the parallel tubes, and by changing a ratio of an inner and outer diameter of at least a portion of the parallel tubes; and wherein a simulation is performed to determine the at least one of the axonal loss or the myelin degradation as a function of at least one of a tortuosity of the extra-axonal space (EAS) or axonal water fraction (AWF) relative to one or more axonal geometries.

33. A system for determining at least one of axonal loss or myelin degradation, comprising:
   a computer hardware arrangement configured to:
      determine at least one of a measure of diffusion in an extra-axonal space or a measure of a density of axons; and
      determine the at least one of the axonal loss or the myelin degradation using the at least one of the measure of the diffusion in the extra-axonal space or the measure of the density of axons based on axonal geometry of a plurality of parallel tubes
      wherein neurodegeneration is reflected by a reduction in a number of the parallel tubes, and by changing a ratio of an inner and outer diameter of at least a portion of the parallel tubes; and
      wherein a simulation is performed to determine the at least one of the axonal loss or the myelin degradation as a function of at least one of a tortuosity of the extra-axonal space (EAS) or axonal water fraction (AWF) relative to one or more axonal geometries.

* * * * *

UNITED STATES PATENT AND TRADEMARK OFFICE
CERTIFICATE OF CORRECTION

PATENT NO. : 9,916,654 B2
APPLICATION NO. : 14/358785
DATED : March 13, 2018
INVENTOR(S) : Els Fieremans and Dmitry S. Novikov It is certified that error appears in the above-identified patent and that said Letters Patent is hereby corrected as shown below:

In the Specification

Column 1, Line 15, please add the following paragraph:
STATEMENT REGARDING FEDERALLY SPONSORED RESEARCH
This invention was made with government support under grant number R01 NS088040 awarded by the National Institutes of Health. The government has certain rights in this invention.

Signed and Sealed this
Fifth Day of May, 2020

Andrei Iancu
*Director of the United States Patent and Trademark Office*